US011200672B2

(12) United States Patent
Cranmer et al.

(10) Patent No.: US 11,200,672 B2
(45) Date of Patent: Dec. 14, 2021

(54) SYSTEMS AND METHODS FOR MODELING NEURAL ARCHITECTURE

(71) Applicants: Ohio State Innovation Foundation, Columbus, OH (US); The Penn State Research Foundation, University Park, PA (US); University of North Carolina, Chapel Hill, NC (US); University of San Francisco, San Francisco, CA (US)

(72) Inventors: Skyler Cranmer, Columbus, OH (US); Bruce Desmarais, University Park, PA (US); Shankar Bhamidi, Chapel Hill, NC (US); James Wilson, San Francisco, CA (US); Matthew Denny, University Park, PA (US); Zhong-Lin Lu, Columbus, OH (US); Paul Stillman, Columbus, OH (US)

(73) Assignees: Ohio State Innovation Foundation, Columbus, OH (US); The Penn State Research Foundation, University Park (PA); University of North Carolina, Chapel Hill, NC (US); University of San Francisco, San Francisco, CA (US)

( * ) Notice: Subject to any disclaimer, the term of this patent is extended or adjusted under 35 U.S.C. 154(b) by 0 days.

(21) Appl. No.: 17/193,911

(22) Filed: Mar. 5, 2021

(65) Prior Publication Data

US 2021/0209761 A1    Jul. 8, 2021

Related U.S. Application Data

(62) Division of application No. 16/332,280, filed as application No. PCT/US2017/051343 on Sep. 13, 2017, now Pat. No. 11,062,450.

(Continued)

(51) Int. Cl.
*G06T 7/00* (2017.01)
*A61B 5/026* (2006.01)
(Continued)

(52) U.S. Cl.
CPC .......... *G06T 7/0014* (2013.01); *A61B 5/0263* (2013.01); *A61B 5/369* (2021.01);
(Continued)

(58) Field of Classification Search
CPC ......... G06T 7/0014; G06T 2207/30016; A61B 5/369; A61B 5/0263; A61B 5/7267;
(Continued)

(56) References Cited

U.S. PATENT DOCUMENTS 9,265,441 B2   2/2016   Pereira
9,737,230 B2   8/2017   Sarma
(Continued)

FOREIGN PATENT DOCUMENTS

CN    102360501 A    2/2012
WO    2015175053 A2  11/2015

OTHER PUBLICATIONS

Bian, J., et al., "A Probabilistic Model of Functional Brain Connectivity Network for Discovering Novel Biomarkers," AMIA Joint Summits on Translational Science Proceedings, 2013; 2013: 21-25, published Mar. 2013.*

(Continued)

*Primary Examiner* — Xuemei G Chen
(74) *Attorney, Agent, or Firm* — Benesch, Friedlander, Coplan & Aronoff LLP

(57) ABSTRACT

Systems and methods are described herein for modeling neural architecture. Regions of interest of a brain of a subject can be identified based on image data characterizing the brain of the subject. the identified regions of interest can be mapped to a connectivity matrix. The connectivity matrix (Continued)

can be a weighted and undirected network. A multivariate transformation can be applied to the connectivity matrix to transform the connectivity matrix into a partial correlation matrix. The multivariate transformation can maintain a positive definite constraint for the connectivity matrix. The partial correlation matrix can be transformed into a neural model indicative of the connectivity matrix.

12 Claims, 8 Drawing Sheets

Related U.S. Application Data

(60) Provisional application No. 62/393,949, filed on Sep. 13, 2016.

(51) Int. Cl.
| | |
|---|---|
| *A61B 5/00* | (2006.01) |
| *A61B 5/369* | (2021.01) |
| *G06F 17/16* | (2006.01) |
| *G06F 17/18* | (2006.01) |
| *G06K 9/62* | (2006.01) |
| *G01R 33/563* | (2006.01) |
| *G01R 33/48* | (2006.01) |
| *G01R 33/56* | (2006.01) |

(52) U.S. Cl.
CPC .......... *A61B 5/4064* (2013.01); *A61B 5/7267* (2013.01); *G06F 17/16* (2013.01); *G06F 17/18* (2013.01); *G06K 9/6226* (2013.01); *G01R 33/4806* (2013.01); *G01R 33/5608* (2013.01); *G01R 33/56341* (2013.01); *G06T 2207/30016* (2013.01)

(58) Field of Classification Search
CPC ....... A61B 5/4064; G06F 17/16; G06F 17/18; G06K 9/6226; G01R 33/56341; G01R 33/4806; G01R 33/5608; G16H 50/70
See application file for complete search history.

(56) References Cited

U.S. PATENT DOCUMENTS

| | | | |
|---|---|---|---|
| 9,740,946 B2 | 8/2017 | Varkuti | |
| 9,773,308 B2 | 9/2017 | Silbersweig | |
| 10,201,280 B2 | 2/2019 | Yamagata | |
| 10,357,181 B2 | 7/2019 | Morimoto | |
| 10,672,126 B2 | 6/2020 | Yui | |
| 11,037,296 B1* | 6/2021 | Sughrue | G06T 7/0016 |
| 2003/0096606 A1 | 5/2003 | Inman | |
| 2006/0074290 A1* | 4/2006 | Chen | G06T 7/0012 |
| | | | 600/407 |
| 2011/0137851 A1* | 6/2011 | Cavet | G01N 33/53 |
| | | | 706/54 |
| 2011/0190621 A1 | 8/2011 | Verdoorn | |
| 2011/0301431 A1 | 12/2011 | Greicius | |
| 2012/0015381 A1* | 1/2012 | Neuman | G01N 33/6896 |
| | | | 435/7.92 |
| 2013/0123607 A1 | 5/2013 | Leuthardt | |
| 2013/0231552 A1 | 9/2013 | Grady | |
| 2014/0107521 A1 | 4/2014 | Galan | |
| 2014/0121554 A1 | 5/2014 | Sarma | |
| 2014/0222738 A1* | 8/2014 | Joyce | G06N 3/10 |
| | | | 706/13 |
| 2015/0294074 A1* | 10/2015 | Kawato | G16H 50/20 |
| | | | 702/19 |
| 2015/0324994 A1 | 11/2015 | Tseng | |
| 2016/0158240 A1 | 6/2016 | Crozier | |
| 2016/0210552 A1 | 7/2016 | Kasabov et al. | |
| 2016/0287118 A1 | 10/2016 | Sarma | |
| 2016/0300352 A1 | 10/2016 | Raj | |
| 2017/0052241 A1* | 2/2017 | Cetingul | A61B 5/0042 |
| 2017/0220900 A1* | 8/2017 | Boada | G06K 9/6247 |
| 2017/0367607 A1* | 12/2017 | Agarwal | G06K 9/00496 |
| 2018/0199848 A1 | 7/2018 | Wendling | |
| 2018/0279939 A1* | 10/2018 | Madsen | A61B 5/4094 |
| 2019/0059769 A1 | 2/2019 | Nenadovic | |
| 2019/0133446 A1 | 5/2019 | Emerson | |
| 2019/0167177 A1* | 6/2019 | Evins | A61B 5/7267 |
| 2019/0180636 A1 | 6/2019 | Lei | |
| 2019/0254585 A1 | 8/2019 | Jirsa | |
| 2020/0163609 A1 | 5/2020 | Lisi | |

OTHER PUBLICATIONS

International Search Report in International Application No. PCT/US2017/051343, dated Jan. 5, 2018 (5 pages).

Written Opinion in International Application No. PCT/US2017/051343, dated Jan. 5, 2018 (8 pages).

Zuendorf et al., "Efficient Principal Component Analysis for Multivariate 3D Voxel-Based Mapping of Brain Functional Imaging Data Sets as Applied to FDG-PET and Normal Aging," Human Brain Mapping, vol. 18, 2003, pp. 13-21 (12 pages).

Lohmann, G. et al., "Eigenvector Centrality Mapping for Analyzing Connectivity Patterns in fMRI Data of the Human Brain," PLoS One, vol. 5, Issue 4, Apr. 2010, pp. 1-8 (8 pages).

Cordes, D. et al., "Mapping Functionally Related Regions of Brain with Functional Connectivity MR Imaging," American Journal of Neuroradiology, vol. 21, Oct. 2000, pp. 1636-1644 (9 pages).

Desmarais, B.A. et al., "Statistical Inference for Valued-Edge Networks: The Generalized Exponential Random Graph Model," PLoS One, vol. 7, Issue 1, Jan. 2012, pp. 1-12 (12 pages).

Venkataraman, A. et al., Joint Modeling of Anatomical and Functional Connectivity for Population Studies, IEEE Transactions on Medical Imaging, vol. 31, No. 2, Feb. 2012, pp. 164-182 (23 pages).

Fallani, F. et al., "Graph analysis of functional brain networks: practical issues in translational neuroscience," Philosophical Transactions of the Royal Society B, Jun. 28, 2014, downloaded at <file:///C:/Users/evely/Documents/Landon%20IP/17-51343.%20due%2012-11/FALLANI%20et%20al.pdf> (36 pages).

Varoquaux, G. et al. "Learning and comparing functional connectomes across subjects," NeuroImage, vol. 80, Apr. 2013, pp. 405-415 (11 pages).

\* cited by examiner

SYSTEMS AND METHODS FOR MODELING NEURAL ARCHITECTURE

CROSS-REFERENCE TO RELATED APPLICATIONS

This application is a divisional application of U.S. patent application Ser. No. 16/332,280 titled "SYSTEMS AND METHODS FOR MODELING NEURAL ARCHITECTURE", filed on Mar. 11, 2019, which is a U.S. national stage entry of International Application No. PCT/US17/51343, filed on Sep. 13, 2017, entitled "SYSTEMS AND METHODS FOR MODELING NEURAL ARCHITECTURE," which claims the benefit of U.S. Provisional Application No. 62/393,949, filed on Sep. 13, 2016, entitled "SYSTEMS AND METHODS FOR MODELING NEURAL ARCHITECTURE", the contents of which are incorporated herein by reference in their entirety.

GOVERNMENT LICENSE RIGHTS

This invention was made with government support under Grant Nos. SES1619644, SES1357622, SES1357606 and SMA1533500 awarded by the National Science Foundation. The government has certain rights in the invention.

TECHNICAL FIELD

This disclosure generally relates to systems and methods for modeling neural architecture. More specifically, this disclosure relates to systems and methods for inferential testing, network modeling, and network simulation of the neural architecture.

BACKGROUND

The brain is highly dynamic—billions of neurons across hundreds of brain regions interact to give rise to human cognition. Neural activity data can be used to capture the degree of activity between regions of the brain. The neural activity data can be collected from various inspection modalities. For example, functional magnetic resonance imaging (fMRI) images, diffusion tensor imaging (DTI) images, diffusion weighted imaging (DWI) images, electromyogram (EMG), electroencephalogram (EEG), positron emission tomography (PET), magnetoencephalography (MEG), Electrocorticography (ECoG), ultra-sound imaging, and their combination can be collected from brain matter of a patient. However, improvements in the ability to gather neural activity data has outpaced the current analytical capabilities of neuroscience.

Currently, analytical tools are available for analyzing neural activity data. However, existing analytical tools analyze neural activity data without substantially altering the neural activity data prior to testing. Moreover, existing analytic tools for analyzing the neural activity data are limited to the analyses of binary networks in which connections are either "on" (conventionally coded 1) or "off" (conventionally coded 0). Thus, existing tools for the analysis of neural activity data fail to account for the weighted (valued) nature of network connections. In general, both descriptive and inferential analyses include determining a strength value between two regions of the brain (e.g., a correlation strength between −1 and 1; or probability of connection between two regions), and generating a binary (on or off) connection based on a threshold. Thus, such analyses only consider connections between regions of the brain that exceed the threshold. Thus, analysis of neural activity data, both descriptive and inferential, fail to effectively utilize information captured by the neural activity data on the relative strength of connections between regions of the brain. Moreover, analysis of these dichotomized neural activity networks does not allow for evaluation of strong and weak connections relative to one another, and fails to account for negative connections (e.g., inhibitory connections). Additionally, the threshold can be subjective, with little or no theory informing the value of the threshold. Furthermore, the use of different thresholds can lead to qualitatively different results.

Neural activity data can be evaluated according to graph theory. Graph theory can be used to quantify structural and functional networks. In general, the brain or some subset thereof can be divided into a series of nodes (e.g., individual voxels, or clusters of voxels). A connectivity matrix can be created by evaluating a connection strength between the series of nodes. The information encoded in the connectivity matrix is thresholded with individual correlation values rounded to zero or one to create an adjacency matrix of dichotomous connections, or continuous ties. A number of different statistics can be applied to constructed networks to assess both network structure and the roles of individual nodes within the network. The metrics can be compared between individuals, tasks, or both, to quantify network structural shifts. However, thresholding and a lack of statistical power, stand in the way of fully utilizing the information provided by neural activity data.

SUMMARY

In an example, a computer-implemented method for modeling neural architecture can include identifying, by one or more processors, regions of interest of a brain of a subject based on image data characterizing the brain of the subject. The computer-implemented method can further include mapping, by the one or more processors, the regions of interest to a connectivity matrix. The connectivity matrix can be a weighted and directed or undirected network. The computer-implemented method can further include applying, by the one or more processors, a multivariate transformation to the connectivity matrix to transform the connectivity matrix into a partial correlation matrix. The multivariate transformation can maintain a positive definite constraint for the connectivity matrix. The computer-implemented method can further include transforming, by the one or more processors, the partial correlation matrix into a neural model indicative of the connectivity matrix.

In another example, a computer-implemented method can include identifying, by one or more processors, regions of interest of a brain of a subject based on image data. The image data can include one of magnetic resonance imaging (MRI) data, functional magnetic resonance imaging (fMRI) data, diffusion tensor imaging (DTI) data, diffusion weighted imaging (DWI) data, electromyogram (EMG) data, electroencephalogram (EEG) data, positron emission tomography (PET) data, magnetoencephalography (MEG) data, Electrocorticography (ECoG) data, ultra-sound imaging data, and a combination thereof. The computer implemented method can further include, mapping, by the one or more processors, the regions of interest of the image data to a connectivity matrix. The connectivity matrix can be a weighted and directed or undirected network. The computer-implemented method can further include transforming, by the one or more processors, the connectivity matrix into a biomarker parameter. The biomarker parameter can correspond to a defined statistic. The computer-implemented method can further include analyzing, by the one or more processors, the biomarker parameter according to a probability density function of a statistical cognitive model. The probability density function can map a separate population of the biomarker parameter to a cognitive phenomenon. The computer-implemented method can further include generating, by the one or more processors, a probability of the cognitive phenomenon based on the probability density function of the statistical cognitive model. The probability can quantify a severity of the cognitive phenomenon.

In another example, a method can include receiving, at one or more processors, image data of a subject. The image data can correspond to MRI image data. The method can further include, transforming, at the one or more processors, the image data with a neural modeling engine into a biomarker parameter. The biomarker parameter can correspond to a defined statistic. The method further includes analyzing, at the one or more processors, the biomarker parameter with a probability density function of a statistical cognitive model. The probability density function can map a separate population of the biomarker parameter to a cognitive phenomenon. The method can further include generating, at the one or more processors, an initial probability of the cognitive phenomenon based on the probability density function of the statistical cognitive model. The method can further include quantifying, at the one or more processors, a severity of the cognitive phenomenon for the subject based upon the initial probability.

In an even further example, a method can include transforming, at one or more processors, a connectivity matrix based on a statistic or set of statistics determined based on the connectivity matrix to a descriptive statistical summary characterizing the connectivity matrix. The method can further include classifying, by the one or more processors, a severity and type of cognitive phenomenon present in a subject based on a result of the comparison to a greater population of descriptive summaries of connectivity matrices.

DETAILED DESCRIPTION

Systems and methods are described herein for modeling neural architecture.

Figure 1:
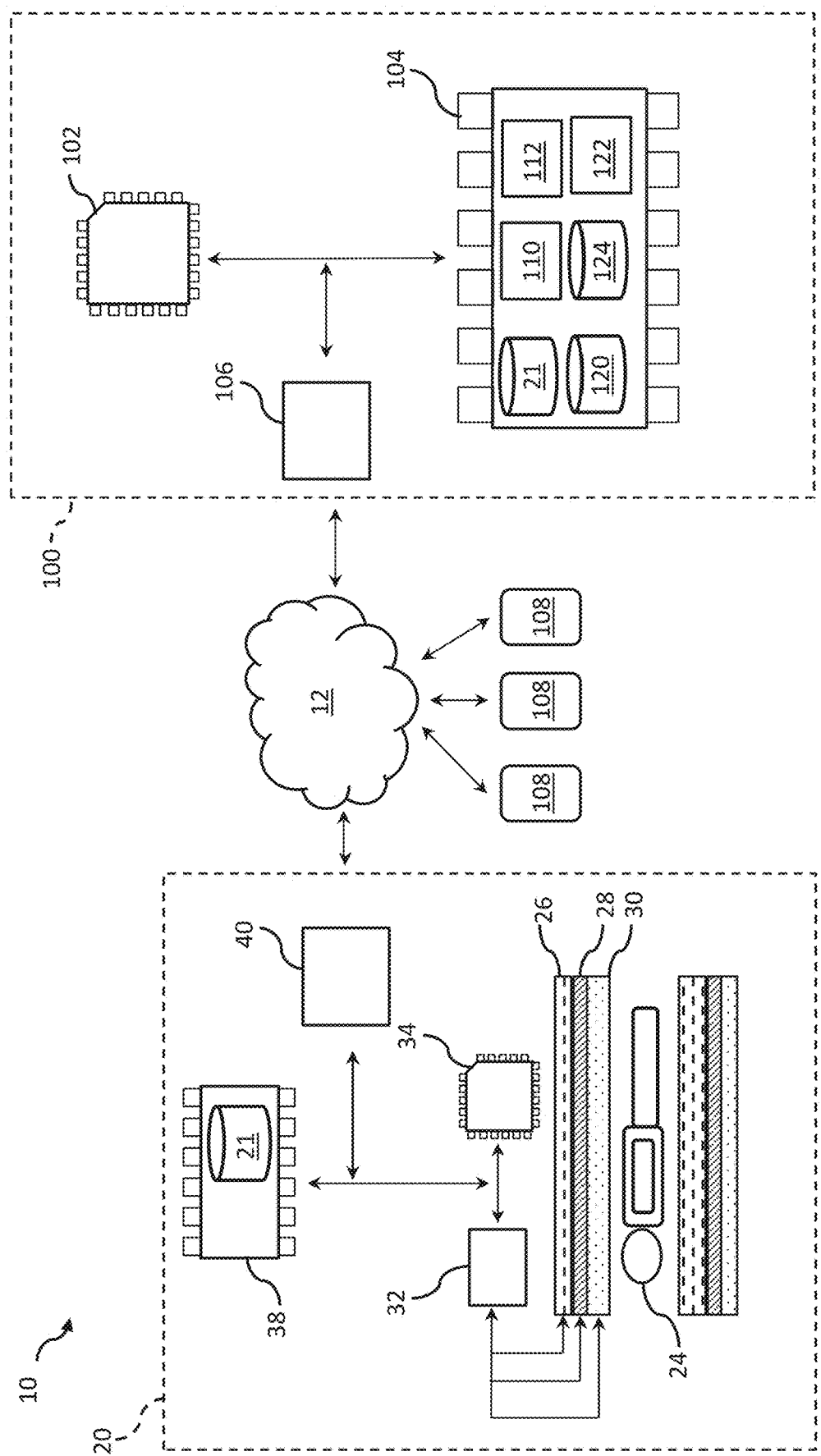
FIG. 1 depicts an example of a system for modeling neural architecture.

FIG. 1 illustrates a system 10 for modeling neural architecture. The system 10 can include an imaging device 20. The imaging device 20 can be configured to generate neural activity data 21 characterizing neural connectivity of a subject 24. The subject 24 can correspond to a human, an animal, or the like. In an example, the imaging device 20 can include a magnetic resonance imaging (MRI) scanner 22. The MRI scanner 22 can be configured to collect signals emitted from atomic nuclei of the subject 24, and to generate images indicative of at least a portion of the subject 24 based on the collected signals. As described herein, the generated images can correspond to the neural activity data 21. FIG. 1 illustrates neural activity data 21 being provided based on images generated by the MRI scanner 22. However, it should be construed that any neural activity technology (e.g., imaging technology) can be used that can produce either functional connectivity or structural connectivity data for the patient 24. Accordingly, any device that can provide neural activity data 21 for the patient 24 based on captured images indicative of at least the portion of the subject 24 can be used.

The MRI scanner 22 can be configured to provide magnetic field signals with a controlled field gradient, and to emit radio frequency (RF) signals that can interact with the atomic nuclei of the subject 24. The MRI scanner 22 can include a magnet 26. The magnet 26 can be configured to generate magnetic field signals that can be applied to the subject 24. A magnetic moment of the atomic nuclei of the subject 24 can substantially align with a direction of the magnetic field based on the magnetic field signals. The MRI scanner 22 can further include gradient coils 28. The gradient coils 28 can be configured to vary a magnitude of the magnetic field signals along one or more gradient directions with respect to the subject 24. The atomic nuclei of the subject 24 can include a resonance frequency that can be proportional to the magnitude of the magnetic field signals. The resonant frequency can depend on a position along each of the one or more field gradients in response to an application of the one or more field gradients.

The MRI scanner 22 can further include RF coils 30. The RF coils 30 can be configured to apply RF signals to the subject 24, and to receive signals emitted by the subject 24. In an example, the RF signals can be transmitted at the resonant frequency of a spatial location along one of the field gradients. Thus, the atomic nuclei at the spatial location can change a corresponding magnetization alignment relative to the magnetic field. Upon cessation of the RF signals by the RF coils 30, the magnetic field can urge the atomic nuclei back to a previous magnetization alignment. As a result of varying the corresponding magnetization alignment, the atomic nuclei of the subject 24 can emit signals (e.g., a varying magnetic flux). The RF coils can detect the emitted signals as a changing voltage.

The MRI scanner 22 can further include signal conditioning hardware 32. The signal conditioning hardware 32 can be coupled to the gradient coils 28 and the RF coils 30. The signal conditioning hardware 32 can be configured to provide driving signals to the gradient coils 28 and the RF coils 30. Additionally, or alternatively, the signal conditioning hardware 32 can be configured to process the emitted signals detected by the RF coils 30.

Figure 2:
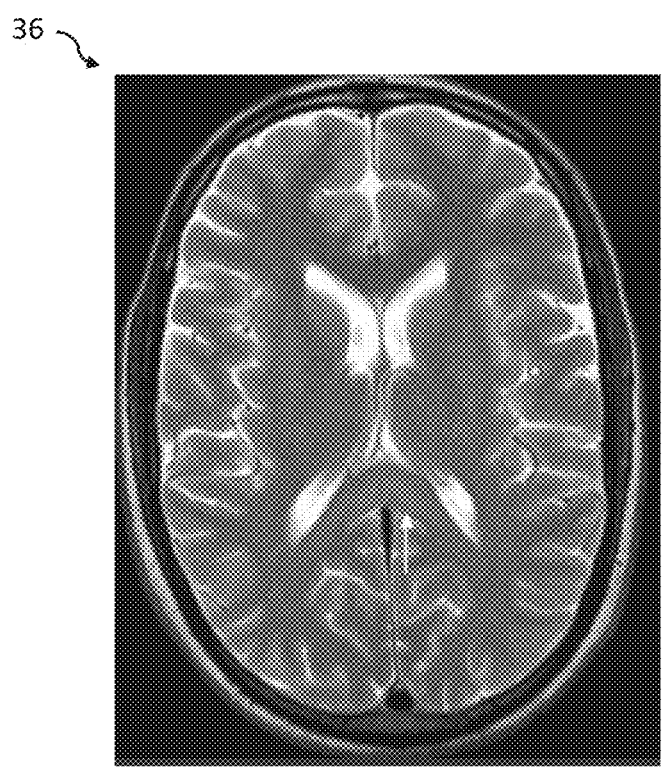
FIG. 2 depicts an example of magnetic resonance imaging (MRI) data.

The MRI scanner 22 can further include one or more processors 34. As used herein, the term "processor" can include any device that can be configured to executing machine readable instructions. The one or more processors 34 can be configured to receive the emitted signals from the conditioning hardware 32. Thus, the one or more processors 34 can be configured to receive processed emitted signals. The one or more processor 34 can further be configured to generate the neural activity data 21 based on the emitted signals. In an example, the neural activity data 21 can correspond to MRI image data 36, such as illustrated in FIG. 2. In this example, the MRI image data 36 can be generated by the MRI scanner 22, as described herein. The MRI image data 36 can include MRI images, functional magnetic resonance imaging (fMRI) images, diffusion tensor imaging (DTI) images, diffusion weighted images (DWI), a combination thereof, or the like.

The fMRI images can be used to providing mapping of active neurons within the brain of the subject 24. In particular, neural activity associated with the brain of the subject 24 can be correlated with blood flow and blood oxygenation in the brain. As neurons become active, oxygenated blood can flow into the neuron and displace deoxygenated blood. Since oxygenated blood and deoxygenated blood can interact differently with magnetism, the signals emitted by the subject 24 can be correlated to blood oxygenation, and thus, neural activity. Additionally, multiple fMRI images can be captured over time to map neural response to stimulus.

In DTI and DWI images, a rate of diffusion of a moiety (e.g., water) can be encoded in an intensity of each component of an image (e.g., voxel). During collection of emitted signals from the subject 24, a sufficient number of field gradients can be applied along gradient directions to calculate a tensor, which can be indicative of the diffusion, for each component. The diffusion can be correlated to a structure of the brain of the subject 24, e.g., the structure can cause the diffusion to have a directional preference. For instance, the structure of axons and myelin sheaths can be preferential to diffusion along a primary direction of the axons and myelin sheaths.

The data can further come from other brain imaging modalities such as electroencephalogram (EEG) data, positron emission tomography (PET), magnetoencephalography (MEG), Electrocorticography (ECoG), electromyogram (EMG) data, and ultra-sound imaging. In EEG, electrodes can be placed on the subject's scalp to measure electrical potentials generated by the brain. ECoG is similar, except the electrodes can be placed directly on exposed brain (e.g., if the scalp has been temporarily removed for a medical procedure). In MEG, magnetic fields can be recorded from the brain via magnetometers. In PET, radioactive metabolic chemicals (e.g., glucose) can be injected into the subject's bloodstream, and a corresponding emission from the radioactive metabolic chemicals can be subsequently measured to provide an indication of where the brain is using these chemicals.

The imaging device 20 can further include memory 38. The neutral activity data 21 can be stored in the memory 38. The memory 38 can be coupled to the one or more processors 34. The one or more processors 34 can be configured to retrieve the neutral activity data 21 stored in the memory 38. The memory 104 can be implemented, for example, as a non-transitory computer storage medium, such as volatile memory (e.g., random access memory), non-volatile memory (e.g., a hard disk drive, a solid-state drive, flash memory or the like), or a combination thereof.

The imaging device 20 can further include network interface hardware 40. The network interface hardware 40 can be configured to couple the imaging device 20 to another device over a network 12. The network can include one of a wide area network (WAN), a local area network (LAN), personal area network (PAN), and combination thereof. The network interface hardware 40 can be configured to communicate, e.g., send and/or receive data via a wired or wireless communication protocol based on the network 12. For example, the network interface hardware 40 can include at least one of an antenna, a modem, LAN port, wireless fidelity (Wi-Fi) card, WiMax card, near-field communication hardware, and the like, that can be configured to facilitate the sending and/or receiving of data to and from the imaging device 20. Thus, the imaging device 20 can be coupled to the network 12 via physical wires, via a WAN, via a LAN, via a PAN, via a satellite network, or the like.

The system 10 can further include a neural architecture system 100. The neural architecture system 100 can be configured to execute machine readable instructions to provide inferential testing, network modeling, and/or network simulation of neural architecture based on the neural activity data 21. In an example, the neural architecture system 100 can be implemented on a computer, a server, or the like. The neural architecture system 100 can include one or more processors 102. The one or more processors 102 can be coupled to memory 104 of the neural architecture system 100. The one or more processors 102 can further be coupled to a network interface hardware 106 of the neural architecture system 100. In the present example, although the components of the neural architecture system 100 are illustrated as being implemented on the same system, in other examples, the different components could be distributed across different systems and communicate, for example, over the network 12.

The neural architecture system 100 can be configured to be communicate with one or more client devices 108 over the network 12. Each of the one or more client devices 108 can include memory for storing data and machine-readable instructions. The memory can be implemented similar to the memory described herein. The one or more client devices 108 can include a tablet, a mobile device, a laptop, a computer, or the like.

The neural architecture system 100 can further include a neural modeling engine 110. The neural modeling engine 110 can be configured to generate a neural model 112 of the networks within the brain of the subject 24 based on the neural activity data 21. The neural model 112 can include any model that can simulate the neural activity data 21, e.g., the neural model 112 can provide an output that can resemble the neural activity data 21. The neural modeling engine 110 can include an algorithm. The algorithm can include, one of a deterministic algorithm, a probabilistic algorithm that does not account for network interdependencies, and probabilistic algorithm that does account for network interdependencies. The algorithm can be applied to the neural activity data 21 to generate the neural model 112.

Many current approaches treat the neural activity data 21 as a matrix of correlation values, which is necessarily undirected. While the descriptive and inferential methods described herein are applicable to correlation networks, many of the descriptive and inferential examples described herein are similarly applicable to directed networks. For examples, techniques such as Granger Causality and Bayesian Network Analysis can both produce estimates of the directed influence of one node on another, as opposed to a single number reflecting the connection between two nodes. The examples described herein are equally adaptable to either data format.

A node-level algorithm can specify a fixed degree distribution for the nodes of the brain and generate simulated networks based on the fixed degree distribution. A probabilistic algorithm, which does not account for network interdependencies, can include linear regression, which can include exogenous or dyadic endogenous factors as inputs, and can use predicted edge values to generate simulated networks. A probabilistic algorithm, which can account for network interdependencies, can take endogenous (e.g., network) and exogenous dependencies as inputs and can generate simulations of neural networks based on estimated parameters corresponding to the inputs.

In some example, the neural modeling engine 110 can include a neurological generalized exponential random graph model (neuro-GERGM) algorithm. The neuro-GERGM algorithm can be classified as a probabilistic algorithm, which can account for network interdependencies. The neuro-GERGM technique can create a joint probability distribution by evaluating a set of interdependencies between nodes of the brain, which can be specified as statistics on the network of interest. The joint probability distribution can be used to evaluate the estimated parameter values of interest, and simulate neural networks that can include a similar resemblance to the neural activity data 21.

The neuro-GERGM algorithm can be considered as a distinctive member of a similar class as exponential random graph models (ERGM) and generalized exponential random graph models (GERGM). ERGMs can provide for inferential analysis of networks. ERGMs are generative models of networks in which a user can define processes, both endogenous to the structure of the network, and exogenous to the structure of the network, which can give rise to the network's structure of connectivity. Given a set of user-defined network statistics that can be specified to capture generative features of the network, the ERGM can fit parameters according to a maximum likelihood. The ERGM model can allow for the inferential testing of hypotheses about which exogenous predictors and endogenous structures generated the data. Inferential testing can provide more analytic analysis than descriptive analyses.

For example, the ERGM model can characterize an observed network as a function of triadic closure—the degree to which having strong connections with two different regions makes those regions likely to be strongly connected. The model can be configured to estimate parameters for each defined statistic, resulting in a set of parameters that can maximize the likelihood of observing the given network. The model can further be configured to generate simulated networks, for use in evaluating model fit or testing counterfactuals about alternative structure of the networks or values of predictors.

An ERGM framework can be limited by the requirement of non-negative integer networks in which connections are limited to integer counts. Thus, ERGM frameworks can include similar drawbacks experienced by other approaches that can include thresholding the network (e.g., excluding information about negative ties or fractional weights). Second, ERGM networks can provide poorly fitted models due to a lack of statistics currently available for neuroscience. As described herein, a neuro-GERGM framework does not require any censoring or thresholding, and can be used to produce substantially well-fitted models to the neural activity data 21 in contrast to the ERGM framework. Moreover, the neuro-GERGM framework can simulate networks according to model parameters that maintain the structure of the neural activity data 21.

In a related example, the neural activity data 21 can be summarized by a statistic that can be computed on the network and can be descriptive rather than inferential. These descriptive statistics can relate to a location or prominence of a particular node of the network, to the relationship between two nodes, or to the connectivity, clustering, diameter, or other properties of the network. An example of a statistic capturing the prominence of a node is Eigenvector centrality. For a network composed of a set of nodes/vertices V and a set of edge values connecting them E, the matrix A can be defined such that $A_{ij}$ captures the value of vertex i's connection to vertex j. The eigenvector centrality of vertex i can be defined as:

$$c_{e_i}(v) = \alpha \sum_{\{u,v\} \in E} c_{e_i}(u) \qquad \text{(Equation 1)}$$

where the vector $c_{e_i} = (c_{e_i}(1), \ldots, c_{e_i}(N_v))^T$ can be a solution to the eigenvalue problem $Ac_{e_i} = \alpha^{-1} c_{e_i}$.

The optimal choice of $\alpha^{-1}$ is a greatest eigenvalue of A and hence $c_{e_i}$ is a corresponding eigenvector. The absolute values of these entries can be reported, which can be automatically be on the [0,1] interval by the orthonormality of eigenvectors. An example of a descriptive statistic pertaining to the relationship between two nodes is the path length between said respective nodes. An alternative example is a measure of structural equivalence. An example of a descriptive statistic on the network could be a related clustering coefficient (e.g., the census of closed triads on the network) or a related diameter (e.g., the longest shortest path in the network).

In the foregoing example, the statistics that can describe the neural activity data 21 can be used, absent the neural model 112, to classify cognitive phenomena and measure a corresponding severity. In this example, a given descriptive statistic or set of statistics computed for the subject 24 can be compared by the one or several processors 102 to a reference distribution of other individuals for that same statistic or set of statistics. Based on where the subject 24 falls relative to the reference distribution, a cognitive phenomenon can be indicated and the distance or some other measure between the descriptive statistical value for the subject 24 and some measure of the center or central area of the reference distribution can be used to measure the severity of the cognitive phenomenon.

The GERGM is an exponential family of probability distributions that can be used to characterize the process of graphs with continuous-valued edges. For example, y can be considered a vector of length m=20(20−1)/2 (e.g., a number of undirected edges contained in the modeled network), or m=20(20−1) (e.g., a number of directed edges contained in the modeled network) where each entry of y is a real-valued edge weight that describes one connection of the neural activity data 21. It is noted that the vector y can be scaled to fit with the dimensions of the neural activity data 21. A vector x can have a similar length m, whose entries can be bounded between 0 and 1, and can represent the relational structure of the neural activity data 21.

The specification of a GERGM for an observed graph y can proceed in two steps. First, a vector of statistics h(x) of length p<m can be specified to describe the structural patterns of the graph x. The choice of these endogenous (network-level) statistics can be flexible, and can be specified to model any dyadic feature of a weighted graph. Once the statistics have been specified, the bounded network $x \in [0, 1]^m$ can be modeled by a density function:

$$f_X(x | \theta) = \frac{\exp(\theta^T h(x))}{\int_{[0,1]^m} \exp(\theta^T h(z)) dz}, \qquad \text{(Equation 2)}$$

where θ is a p-dimensional vector of parameters that quantifies the effects of the network statistics h(x) on the likelihood of the graph x.

In the second specification step of the GERGM, a cumulative distribution function (CDF) T(•|β): $\mathbb{R}^m \to [0, 1]^m$ can be selected to model a transformation from y to x. The transformation can be parameterized by a vector of q<m real-valued parameters β. The function T(•| β) can be used to model the relationship between the graph y on external, or exogenous, predictors that describe the network. For example, T can be selected as a joint cumulative distribution function (CDF) of independent Gaussian random variables. Accordingly, a linear regression of y on any number of exogenous predictors can be modeled and β can serve as the regression coefficients associated with the exogenous predictors.

Using the transformation function T, the edge weight between distinct nodes i and j can be modeled by the transformation $x_{ij}=T_{ij}(y|\beta)$. By Equation 2, it can follow that the network $y \in \mathbb{R}^m$ can have a joint density function, such as $$f_Y(y|\theta, \beta) = f_X(T(y|\beta)|\theta) \prod_{ij} t_{ij}(y|\beta),$$ (Equation 3)

where $t_{ij}(y|\beta)=dT_{ij}(y|\beta)/dy_{ij}$ is a marginal density function for all i≠j. In the case that there are no structural dependencies (e.g., when θ=0), Equation 3 can be simplified to a regression of y on exogenous predictors.

Figure 3:
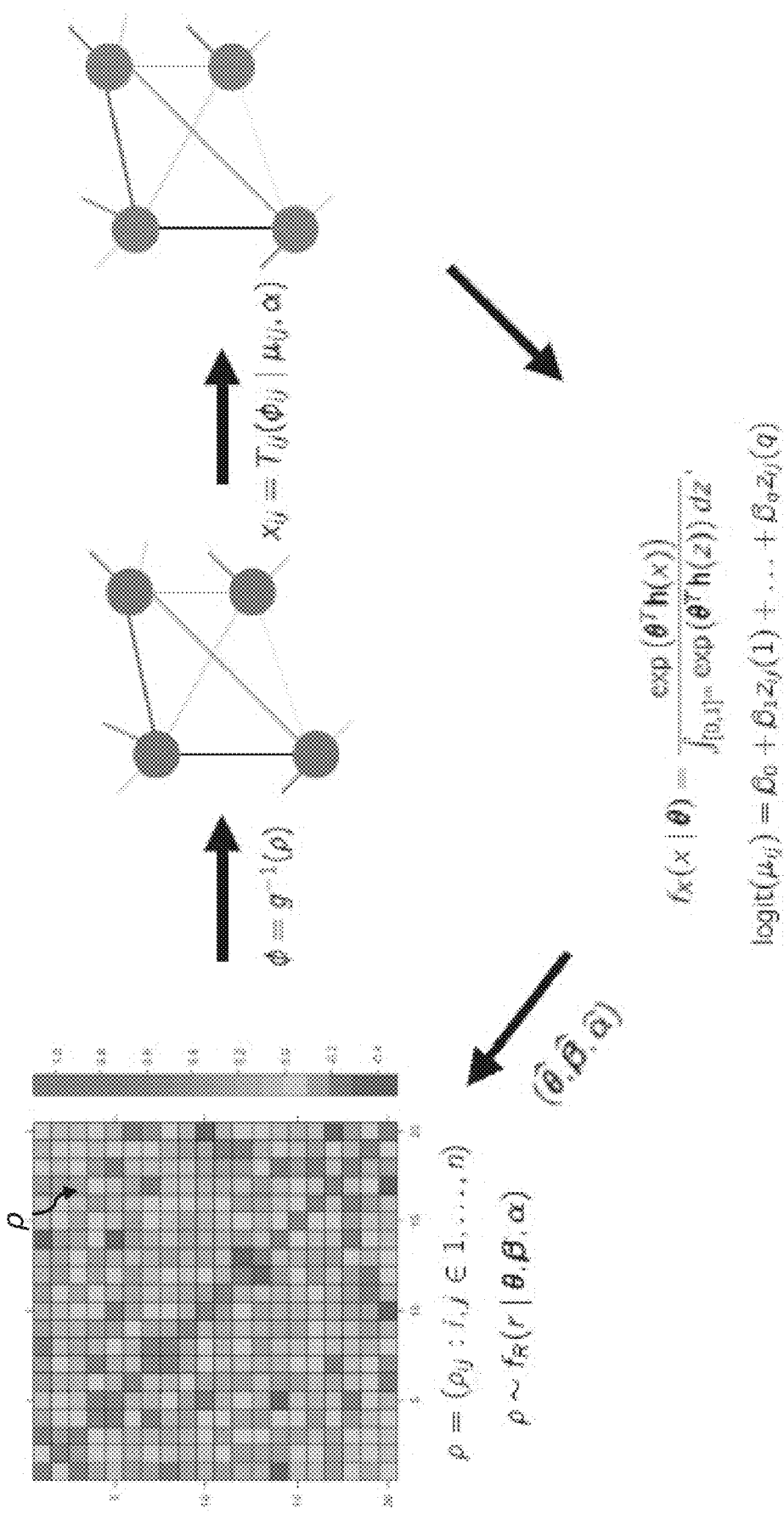
FIG. 3 depicts an example of a process for transforming a connectivity matrix into a neural model.

FIG. 3 depicts an example of a process for transforming a connectivity matrix into a neural model (e.g., the neural model 112, as shown in FIG. 1). As shown in FIG. 3, the GERGM can transform the edges of a connectivity matrix ρ of the neural activity data 21 onto a two-dimensional space, such as a [0, 1] space, and calculate a partial correlation network φ based on the log-likelihood of the structural parameters. Subsequently, the edges of the constrained network can be transformed back to the original space based on a regression on the specified exogenous predictors.

Equation 3 can provide a framework to model the process of weighted graphs. The GERGM framework can be modified to model correlation networks as the neuro-GERGM to analyze the neuronal architecture of functional networks arising based on the neural activity data 21. One difficulty of modeling correlation matrices lies in the fact that correlation matrices must be positive definite. The statistical models for correlation networks should be constructed to account for the constraint of positive definiteness. Unconstrained models offer limited predictive utility, and thus cannot be used to simulate valid correlation matrices. The ERGM framework does not offer models that can generate networks constrained to be positive definite. Moreover, directly analyzing the structural properties of a brain correlation network without accounting for positive definiteness can lead to inferential false positives due to artifacts in the data.

Suppose that ρ is the observed connectivity matrix of the neural activity data 21, ρ can be viewed as a weighted and undirected network whose edge weights can lie between −1 and 1. The neuro-GERGM algorithm can evaluate the pairwise correlations among n regions in the brain arising based on the neural activity data 21. The neural activity data 21 can be represented with an undirected network represented by the weighted symmetric adjacency matrix $\rho=(\rho_{ij}: i, j \in 1, \ldots, n)$. In this example, $\rho_{ij} \in [-1, 1]$ and $\rho_{ij}=\rho_{ij}$ for all i and j. As described herein, the evaluation of ρ applies the constraint of the correlation matrices being positive definite. Thus, for any non-zero vector v of length n, the following relation must hold:

$$v^T \rho v > 0.$$ (Equation 4)

The relation can strongly constrain the values of ρ by including structural dependence between each entry $\rho_{ij}$ and every other entry. Furthermore, for valid inference of ρ, the model should ensure that estimates, for example $\hat{\rho}$, can satisfy Equation 4.

The neuro-GERGM framework can provide a family of models for a random matrix $\rho \in [-1, 1]^{n \times n}$ that can uphold the positive definite constraint of ρ, can characterize the relational (network) structure of ρ, and the relationship between the entries of ρ and a collection of potentially useful regressors $z_1, \ldots, z_q$. For example, to satisfy the positive definite constraint on ρ, a multivariate transformation can be applied to the observed network p to obtain the vector of unconstrained partial correlation values φ. The partial correlation network φ can be normalized, and directly modeled based on the GERGM specification in Equation 3. The resulting graphical model can uphold the positive definite constraint on ρ, and can describe both the endogenous and exogenous features of the observed network.

In particular, ρ can be viewed as an undirected and weighted network whose edge weights ($\rho_{ij}$: i<j∈[n]) lie in $[-1, 1]^{n'}$, where m=n(n−1)/2 is a total number of interactions among the n regions in the brain. The neuro-GERGM framework, similar to the GERGM framework, can begin with characterizing the joint network features of the connectivity matrix ρ based on a constrained network $x \in [0, 1]^m$, which can have an exponential family density function consistent with Equation 2. A vector of unconstrained partial correlations $\phi=(\phi_{ij}: i<j \in [n]) \in [-1, 1]^m$ can be generated based on the transformation $x_{ij}=T_{ij}((\phi+1)/2|\mu_{ij}, \alpha)$, where $T_{ij}(\cdot|\mu_{ij}, \alpha)$ is the CDF of a Beta distribution with mean $\mu_{ij}$ and scale parameter α. Let T: $\mathbb{R}^m \to [0, 1]^m$ can be defined as an m-dimensional vector $T(\phi|\mu, \alpha)=(T_{ij}(\phi_{ij}|\mu_{ij}, \alpha), i<j \in [n])$. A random vector φ form can be generated based on the probability density function (PDF) $f_\phi(\phi|\theta, \mu, \alpha)$:

$$f_\phi(\phi|\theta, \mu, \alpha) = \frac{\exp(\theta^T h(T((\phi+1)/2|\mu, \alpha)))}{2\int_{[0,1]^m} \exp(\theta^T h(z))dz}$$ (Equation 5)

$$\prod_{ij} t_{ij}((\phi+1)/2|\mu_{ij}, \alpha), \phi \in [-1,1]^m;$$

$$t_{ij}(w|\mu_{ij}, \alpha) = \frac{\Gamma(\alpha)}{\Gamma(\mu_{ij}\alpha)\Gamma((1-\mu_{ij})\alpha)} w_{ij}^{\mu_{ij}\alpha-1}(1-w_{ij})^{(1-\mu_{ij})\alpha-1},$$

$$w_{ij} \in (0,1)$$

where $\Gamma(t)=\int_0^\infty x^{t-1}e^{-x}dx$ is a standard gamma function.

Equation 5 can be related to the GERGM formulation of Equation 3, with an exception that T is selected as a joint Beta CDF to account for the domain of the partial correlation values in φ. A notable property of Equation 5 is that when the partial correlation network φ does not contain any network structure, e.g., when θ=0, then the m components of (φ+1)/2 are independent samples from a Beta($\mu_{ij}$, α) distribution, where $\mu_{ij} \in (0, 1)$ is the expected value of $(\phi_{ij}+1)/2$ and a is the precision of the distribution.

Equation 5 can be used to evaluate the effect of exogenous variables $z_1, \ldots, z_q$ on the partial correlation matrix φ. Let $z_{ij}$ be a vector of dyadic observations $z_{ij}$ be a vector of dyadic observations $z_l=(z_{ij}(l):i<j\in[n])$ for $l=1, \ldots, q$. The effect of each predictor can be modeled based on a linear model for the mean $\mu$ of $\phi$:

$$\log it(\mu_{ij})=\beta_0+\beta_1 z_{ij}(1)+ \ldots +\beta_q z_{ij}(q) \quad \text{(Equation 6)}$$

As $\mu_{ij} \in (0, 1)$, the logit (•) link in Equation 5 is an option, but any monotonically increasing and twice differentiable function can be used. The regression model in Equation 6, together with the Beta density $t_{ij}(\bullet|\mu_{ij}, \alpha)$ can be generally referred to as "Beta regression."

The final step of defining the neuro-GERGM framework is based on a relationship between the partial correlation matrix $\phi$ and an associated connectivity matrix $\rho$ for the collection of n brain regions. For instance, $\phi_{j, j+k}$ can denote the partial correlation between region j and j+k given regions $j+1, \ldots, j+k-1$ for $k \geq 2$. One-to-one mapping can be used between $\rho$ and $\phi$. For example, given $\phi$, the connectivity matrix $\rho$ can be computed based on the following recursion:

$$\rho_{j\,j+k} = \begin{cases} 1 & k=0 \\ \phi_{j\,j+k} & k=1 \\ \rho_1^T(j,k)D_{jk}^{-1}\rho_2^T(j,k)+\phi_{j\,j+k}C_{jk} & 2 \leq k \leq n-j, \end{cases} \quad \text{(Equation 7)}$$

where $$\rho_1^T(j,k) = (\rho_{j\,j+1}, \ldots, \rho_{j\,j+k-1}),$$

$$\rho_2^T(j,k) = (\rho_{j+k\,j+1}, \ldots, \rho_{j+k\,j+k-1}),$$

$$C_{jk}^2 = [1-\rho_1^T(j,k)D_{jk}^{-1}\rho_1^T(j,k)]$$

$$[1-\rho_2^T(j,k)D_{jk}^{-1}\rho_2^T(j,k)], \text{ and}$$

$$D_{jk} = \begin{pmatrix} \rho_{j+1\,j+1} & \rho_{j+2\,j+1} & \cdots & \rho_{j+k-1\,j+1} \\ \rho_{j+1\,j+2} & \rho_{j+2\,j+2} & \cdots & \rho_{j+k-1\,j+2} \\ \vdots & \vdots & \vdots & \vdots \\ \rho_{j+1\,j+k-1} & \rho_{j+2\,j+k-1} & \cdots & \rho_{j+k-1\,j+k-1} \end{pmatrix}$$

The multivariate transformation from $\rho$ to $\phi$ given based on the recursion in Equation 7 can be represented by $\rho=g(\phi)$. Applying the inverse probability transform to the density in Equation 5, a positive definite connectivity matrix $\rho$ can be generated based on the density:

$$D_{jk} = \begin{pmatrix} \rho_{j+1\,j+1} & \rho_{j+2\,j+1} & \cdots & \rho_{j+k-1\,j+1} \\ \rho_{j+1\,j+2} & \rho_{j+2\,j+2} & \cdots & \rho_{j+k-1\,j+2} \\ \vdots & \vdots & \vdots & \vdots \\ \rho_{j+1\,j-1} & \rho_{j+2\,j-1} & \cdots & \rho_{j+k-1\,j+k-1} \end{pmatrix} \quad \text{(Equation 8)}$$

where $|J(c)|$ is the determinant of the Jacobian of the transformation given by:

$$|J(c)| = \left[\prod_{i=1}^{n-1}(1-c_{i\,i+1}^2)^{n-1}\prod_{k=2}^{n-2}\prod_{i=1}^{n-k}(1-c_{i\,i+1}^2)^{n-k-1}\right]^{-1/2} \quad \text{(Equation 9)}$$

Accordingly, for fixed parameters $\theta=(\theta_1, \ldots, \theta_p)$, $\beta=(\beta_0, \ldots, \beta_q)$, and $\alpha>0$, the neuro-GERGM model for a connectivity matrix $\rho$ on n brain regions can be characterized by the following process:

$$\rho \sim f_R(r|\theta, \Theta, \alpha)$$

$$\log it(\mu_{ij})=\beta_0+\beta_1 z_{ij}(1)+ \ldots +\beta_q z_{ij}(q), i<j\in[n] \quad \text{(Equation 10)}$$

To fit a neuro-GERGM model in Equation 10 to an observed connectivity matrix $\rho$, statistics can be defined, computed either on the network of interest or between the network of interest, and another set of values. In an example, the statistics can include two forms: endogenous (network-level) statistics $h(x)=(h_1(x), \ldots, h_p(x))$, and exogenous statistics $z_1, \ldots, z_q$. Accordingly, to fit the neuro-GERGM model, the endogenous predictors can be specified as the vector $h(x)$, the exogenous predictors can be specified for the regression function $T(\bullet|\beta)$, or both. The corresponding vectors of coefficients, $\theta$ and $\beta$, can characterize the effect of the specified statistics on the process of the observed weighted graph.

Endogenous statistics can include statistics for which the derivative of the statistic value with respect to the value of at least one edge in the network depends on the value of at least one other edge in the network. The endogenous statistics can be computed as sums of subgraph products such as, for example, two-stars, transitive triads, or any other statistic suitable to characterize neural activity. The two-stars statistic can measure preferential attachment, which can be higher for networks in which there is a high variance in the popularity of vertices. Two-stars is relevant to neuroscience research in graphs since two-stars can correspond to the degree to which hubs are present in a given network relative to chance, allowing for direct inferential testing of the role of hubs in a given network. Two-stars can quantify the presence of hubs in a network given the importance for hubs in neural networks. Transitive triads (triads) can measure clustering, which can be higher when triads of nodes exhibit higher interconnection between them. As with preferential attachment, clustering has been shown to be highly important component of neural networks, with the brain showing generally a high-degree of clustering. Further, reductions in clustering (in addition to other metrics), have been associated with disease states such as, for example, schizophrenia.

Exogenous statistics can include statistics for which the derivative of the statistic with respect to the value of any edge in the network does not depend on the value of any other edge in the network. Endogenous statistics can include covariates that can allow for specification of specific node, dyad, or network level properties. Specifying covariates can yield a parameter estimate that corresponds to the magnitude of that covariate on strength of edges. At the node level, either categorical or continuous properties can be specified for each node, and then a covariate can be added based on the relationship between node values. For example, a user can define whether nodes are in the left hemisphere, the right hemisphere, or on the midline. The impact of hemisphere use can be modeled as a node-match term, which can code whether two nodes share a property or not. Thus, nodes can be evaluated to determine whether the nodes have stronger connections to nodes in the same hemisphere rather than the opposing hemisphere. At the network level, the nodes located near each other in a physical space can be modeled to determine whether the nodes are more connected than those that are not. For example, a network level covariate in a matrix of the distances between each node. Additionally, or alternatively, the distances can be calculated using Euclidean distance relative to a center of each region of interest (ROI).

Adding in exogenous statistics to the neuro-GERGM framework can provide several advantages. Adding in exogenous covariates can improve the likelihood of model convergence. Additionally, without exogenous covariates, the simulated networks can have similar structure to the observed network, but will not recover specific edges (e.g., nodes will be exchangeable). Moreover, exogenous covariates allow theoretical testing of whether properties of nodes or dyads influence the strength of connectivity between those regions. By including an exogenous covariate, inferential testing of the importance of such a covariate can be provided. Taken together, by combining endogenous and exogenous statistics, the neuro-GERGM framework can be used to model a wide range of network interdependencies in weighted networks.

Referring again to FIGS. 1 and 3, the neural modeling engine 110 can be programmed to transform a connectivity matrix ρ corresponding to the neural activity data 21 into the neural model 112 according to the neuro-GERGM. The connectivity matrix ρ, and the statistics can be provided to the neural modeling engine 110. Estimation of the neuro-GERGM can include the use of approximate computational methods as a result of the computationally intractable normalizing constant in a denominator of Equation 2. In some examples, the Metropolis-Hastings Markov Chain Monte Carlo methodology can be used to calculate the maximum likelihood estimators for the fixed unknown parameters θ and β. The resulting parameter estimates $\hat{\theta}$ and $\hat{\beta}$ can characterize the effects of the endogenous and exogenous statistics on the likelihood of ρ, respectively. These parameter estimates can be used to further explore the nature of the data through simulation and testing.

It is noted that, while an exemplary computational method is described herein with respect to the GERGM, the computational method can also be used for the neuro-GERGM. Given a specification of statistics $h(\bullet)$, transformation function $T^{-1}$, and observations Y=y from Equation 3, the maximum likelihood estimates (MLEs) of the unknown parameters θ and β can be determined, namely values $\hat{\theta}$ and $\hat{\beta}$ that maximize the log likelihood according to:

$$\ell(\theta, \beta \mid \mathcal{Y}) = \qquad \text{(Equation 10)}$$
$$\theta' h(T(\mathcal{Y}, \beta)) - \log C(\theta) + \sum_{ij} \log t_{ij}(\mathcal{Y}, \beta),$$
$$\text{where } C(\theta) = \int_{[0,1]^m} \exp(\theta' h(z)) dz.$$

The maximization of Equation 10 can be achieved through alternate maximization of ρ|θ and θ|β. For example, the MLEs $\hat{\theta}$ and $\hat{\beta}$ can be computed by iterating between the following two steps until convergence. For r≥1, iterate until convergence:

1. Given $\theta^{(r)}$, estimate $\beta^{(r)} \mid \theta^{(r)}$:

$$\beta^{(r)} = \text{argmax}_\beta \left( \theta^{(r)'} h(T(y, \beta)) + \sum_{ij} \log t_{ij}(\mathcal{Y}, \beta) \right). \qquad \text{(Equation 10)}$$

2. Set $\hat{x} = T(y, \beta^{(r)})$. Then estimate $\theta^{(r+1)} \mid \beta^{(r)}$:

$$\theta^{r+1} = \text{argmax}_\theta (\theta' h(\hat{x}) - \log C(\theta)). \qquad \text{(Equation 12)}$$

For fixed θ, the likelihood maximization in Equation 5 can be accomplished numerically using gradient descent. In an example, wherein $t_{ij}$ is log-concave, and h ∘ T is concave in β, a hill climbing algorithm can be used to find the global optimum. To estimate the maximization in Equation 12, which can be a difficult problem to solve due to the intractability of the normalization factor C(θ) the Markov Chain Monte Carlo (MCMC) can be applied. As described herein, θ can be estimated according to the MCMC framework.

Let θ and $\tilde{\theta}$ be two arbitrary vectors in $\mathbb{R}^p$ and let $C(\bullet)$ be defined as in Equation 10. The crux of optimizing Equation 12 based on Monte Carlo simulation relies on the following property of exponential families:

$$\frac{C(\theta)}{C(\tilde{\theta})} = \mathbb{E}_{\tilde{\theta}}[\exp((\theta - \tilde{\theta})' h(X))]. \qquad \text{(Equation 13)}$$

The expectation in Equation 13 cannot be directly computed. However, a first order approximation for this quantity can be given by the first moment estimate:

$$\mathbb{E}_{\tilde{\theta}}[\exp((\theta - \tilde{\theta})' h(X))] \approx \frac{1}{M} \sum_{j=1}^{M} \exp((\theta - \tilde{\theta})' h(x^{(j)})), \qquad \text{(Equation 14)}$$

where $x^{(1)}, \ldots, x^{(M)}$ is an observed sample from pdf $f_X(\bullet, \tilde{\theta})$.

Define $\ell(\theta \mid \hat{x}) := \theta h(\hat{x}) - \log C(\theta)$. Then maximizing $\ell(\theta \mid \tilde{x})$ with respect to $\theta \in \mathbb{R}^p$ is equivalent to maximizing $\ell(\theta \mid \hat{x}) - \ell(\tilde{\theta} \mid \hat{x})$ for any fixed arbitrary vector $\tilde{\theta} \in \mathbb{R}^p$ p. Equations 13 and 14 suggest:

$$\ell(\theta \mid \hat{x}) - \ell(\tilde{\theta} \mid \hat{x}) \approx \qquad \text{(Equation 15)}$$
$$(\theta - \tilde{\theta})' h(\hat{x}) - \log \left( \frac{1}{M} \sum_{j=1}^{M} \exp((\theta - \tilde{\theta})' h(x^{(j)})) \right).$$

An estimate for θ can be calculated by the maximization of (8). The r+1st iteration estimate $\theta^{(r+1)}$ in 5 can be computed based on the Monte Carlo methods. For example, r+1st iteration estimate $\theta^{(r+1)}$ in 5 can be computed by iterating between the following two steps: Given $\beta^{(r)}$, $\theta^{(r)}$, and $\hat{x} = T(y, \beta^{(r)})$.

1. Simulate networks $x^{(1)}, \ldots, x^{(M)}$ from density $f_X(x, \theta^{(r)})$.
2. Update:

$$\theta^{(r+1)} = \qquad \text{(Equation 16)}$$
$$\text{argmax}_\theta \left( \theta' h(\hat{x}) - \log \left( \frac{1}{M} \sum_{j=1}^{M} \exp((\theta - \theta^{(r)})' h(x^{(j)})) \right) \right).$$

Given observations Y=y, the Monte Carlo algorithm described above can require an initial estimate $\beta^{(0)}$ and $\theta^{(1)}$. $\beta_0$ can be initialized using Equation 11 in the case that there are no network dependencies present, namely, $\beta^{(0)} = \text{argmax}_\beta \{\sum_{ij} \log t_{ij}(y, \beta)\}$. $x_{obs} = T(y, \beta_0)$ can be fixed, and the Robbins-Monro algorithm for exponential random graph models can be used to initialize $\theta^{(1)}$. This initialization step can be thought of as the first step of a Newton-Raphson update of the maximum pseudo-likelihood estimate (MPLE) $\theta_{MPLE}$ on a small sample of networks generated from the density $f_X(x_{obs}, \theta_{MPLE})$.

The Monte Carlo algorithm can include a simulation based on the density $f_X(x, \theta^{(r)})$. As this density cannot be directly computed, MCMC methods such as, for example, Gibbs or Metropolis-Hastings samplers, can be used to simulate from $f_x(x, \theta^{(r)})$. The Gibbs sampling procedure can be used in estimating θ by providing the sample of M networks to be used in approximating Equation 15. However, Gibbs sampling procedure can restrict the specification of network statistics h(•) in the GERGM formulation. For example, the use of Gibbs sampling requires that the network dependencies in an observed network y are captured through x by first order network statistics, namely statistics h(•) that are linear in $X_{ij}$ for all i, j∈[n]. A closed-form conditional distribution of $X_{ij}$ given the remaining network, $X_{-(ij)}$ can be computed according this assumption which can be used in Gibbs sampling.

For example, $f_{X_{ij}|X_{-(ij)}}(x_{ij}, \theta)$ can denote the conditional pdf of $X_{ij}$ given the remaining restricted network $X-_{(ij)}$. Consider the following condition on h(x):

$$\frac{\partial^2 h(x)}{\partial x_{ij}^2} = 0, i, j \in [n] \quad \text{(Equation 17)}$$

Assuming that Equation 17 holds (e.g., is true), a closed form expression can be derived for $f_{x_{ij}|x_{-(ij)}}(x_{ij}, \theta)$:

$$f_{X_{ij}|X_{-(ij)}}(x_{ij}, \theta) = \frac{\exp\left(x_{ij}\frac{\theta' \partial h(x)}{\partial x_{ij}}\right)}{\left(\theta' \frac{\partial h(x)}{\partial x_{ij}}\right)^{-1}\left[\exp\left(\theta' \frac{\partial h(x)}{\partial x_{ij}}\right) - 1\right]} \quad \text{(Equation 18)}$$

Let U be uniform on (0, 1). According to the conditional density in (11), values of $x \in \mathbb{R}^m$ can be simulated iteratively by drawing edge realizations of $X_{ij}|X_{-(ij)}$, based on the following distribution:

$$X_{ij} | X_{-(ij)} \sim \frac{\log\left[1 + U\left(\exp\left(\theta' \frac{\partial h(x)}{\partial x_{ij}}\right) - 1\right)\right]}{\theta' \frac{\partial h(x)}{\partial x_{ij}}}, \theta' \frac{\partial h(x)}{\partial x_{ij}} \neq 0 \quad \text{(Equation 19)}$$

When $$\theta' \frac{\partial h(x)}{\partial h_{ij}} = 0,$$

all values in [0,1] are equally likely; thus, $X_{ij}|X_{-(ij)}$ can be drawn uniformly from support [0,1]. The Gibbs simulation procedure can simulate network samples $x^{(1)}, \ldots, x^{(M)}$ from $f_x(x, \theta)$ by sequentially sampling each edge from its conditional distribution according to Equation 19.

Equation 17 can restrict the class of models that can be fit under the GERGM framework. To appropriately fit structural features of a network such as the degree distribution, reciprocity, clustering or assortative mixing, it may be necessary to use network statistics that involve nonlinear functions of the edges. Under Equation 16, nonlinear functions of edges are not permitted—a limitation that may prevent theoretically or empirically appropriate models of networks in some domains. To extend the class of available GERGMs, Metropolis-Hastings can be used.

An alternative and more flexible way to sample a collection of networks based on the density $f_x(x, \theta)$ is the Metropolis-Hastings procedure. The Metropolis-Hastings procedure can include sampling the t+1st network, $x^{(t+1)}$, via a truncated multivariate Gaussian proposal distribution q(•|x$^{(t)}$) whose mean depends on the previous sample $x^{(t)}$ and whose variance is a fixed constant $\sigma^2$.

An advantage of the truncated Gaussian for bounded random variables over the Beta distribution is that it is straightforward to concentrate the density of the truncated Gaussian around any point within the bounded range. For example, a truncated Gaussian with μ=0.75 and σ=0.05 can result in proposals that are nearly symmetric around 0.75 and stay within 0.6 and 0.9. The shape of the Beta distribution can be less amenable to precise concentration around points within the unit interval, which can lead to problematic acceptance rates in the Metropolis-Hastings algorithm.

Sample w can be based on a truncated normal distribution on [a, b] with mean μ and variance $\sigma^2$ (written $W \sim TN_{(a,b)}(\mu, \sigma^2)$) if the PDF of W is given by:

$$g_W(\omega | \mu, \sigma^2, a, b) = \frac{\sigma^{-1}\phi\left(\frac{\omega - \mu}{\sigma}\right)}{\Phi\left(\frac{b - \mu}{\sigma}\right) - \Phi\left(\frac{a - \mu}{\sigma}\right)}, a \leq \omega \leq b \quad \text{(Equation 20)}$$

where $\phi(\cdot|\mu, \sigma^2)$ is the pdf of a N(μ, $\sigma^2$) random variable and Φ(•) is the cdf of the standard normal random variable. The truncated normal density on the unit interval can be represented as $$q_\sigma(\omega|x) = g_w(\omega|x, \sigma^2, 0, 1) \quad \text{(Equation 21)}$$

Equation 21 can correspond to the proposal density. Denote the weight between node i and j for sample t by $x_{ij}^{(t)}$. The Metropolis-Hastings procedure can further include generating sample $x^{(t+1)}$ sequentially according to an acceptance and/or rejection algorithm. The t+1st sample $x^{(t+1)}$ can be generated as follows:

1. For i, j∈[n], generate proposal edge $\tilde{x}_{ij}^{(t)} \sim q_\sigma(w|x_{ij}^{(t)})$ independently across edges.

2. Set $$x^{(t+1)} = \begin{cases} \tilde{x}^{(t)} = (\tilde{x}_{ij}^{(t)})_{i,j\in[n]} & w.p. \quad \rho(x^{(t)}, \tilde{x}^{(t)}) \\ x^{(t)} & w.p. \quad 1 - \rho(x^{(t)}, \tilde{x}^{(t)}) \end{cases} \quad \text{(Equation 22)}$$

where $$\rho(x, y) = \min\left(\frac{f_x(\mathcal{Y} | \theta)}{f_x(\mathcal{Y} | \theta)} \prod_{i,j\in[n]} \frac{q_\sigma(x_{ij} | \mathcal{Y}_{ij})}{q_\sigma(\mathcal{Y}_{ij} | x_{ij})}, 1\right)$$

$$= \min\left(\exp(\theta'(h(\mathcal{Y}) - h(x))) \prod_{i,j\in[n]} \frac{q_\sigma(x_{ij} | \mathcal{Y}_{ij})}{q_\sigma(\mathcal{Y}_{ij} | x_{ij})}, 1\right)$$

The acceptance probability $p(x^{(t)}, \tilde{x}^{(t)})$ can be thought of as a likelihood ratio of the proposed network given the current network $x^{(t)}$ and the current network given the proposal $\tilde{x}^{(t)}$. Large values of $p(x^{(t)}, \tilde{x}^{(t)})$ suggest a higher likelihood of the proposal network. The resulting samples $\{x^{(t)}, t=1, \ldots, M\}$ define a Markov Chain whose stationary distribution is the target pdf $f_x(\cdot|\theta)$.

The proposal variance parameter $\sigma^2$ can influence the average acceptance rate of the Metropolis-Hastings procedure as described above. For example, the value of $\sigma^2$ can be inversely related to the average acceptance rate of the algorithm. In some examples, the proposal variance parameter $\sigma^2$ can be tuned such that the average acceptance rate is a given value, for example, approximately 0.25.

Figure 4:
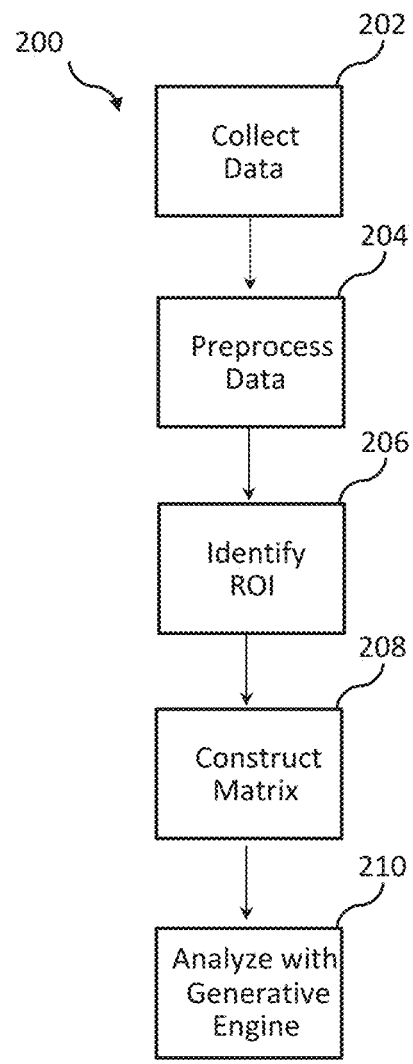
FIG. 4 depicts an example of a flow diagram illustrating an example method for generating a neural model and biomarker parameters.
Figure 7:
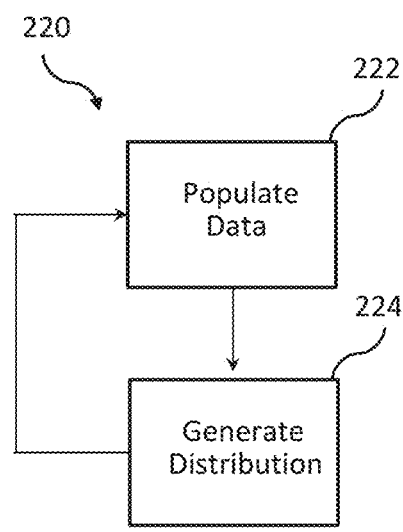
FIG. 7 depicts an example of a flow diagram illustrating an example method for generating a statistical cognitive model
Figure 8:
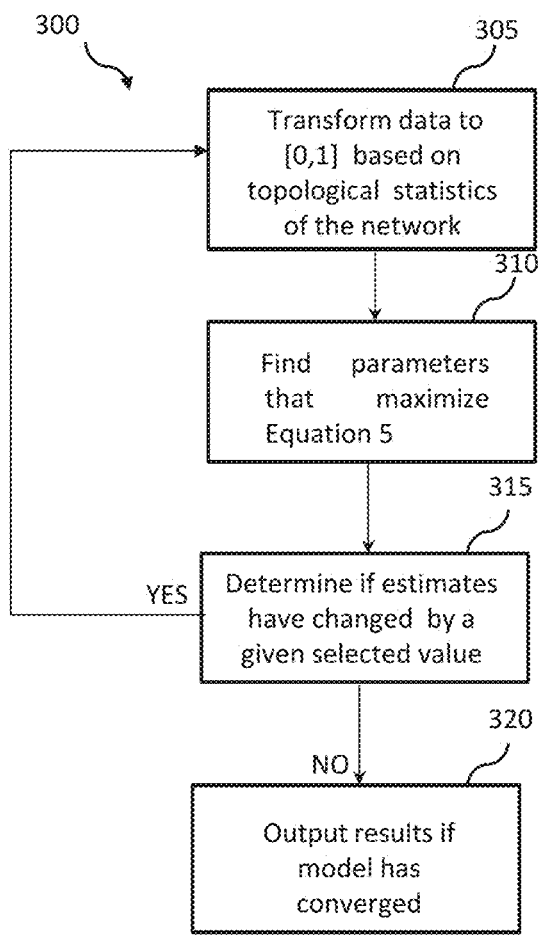
FIG. 8 depicts an example of a flow diagram illustrating an example method for analyzing a connectivity matrix.

In view of the foregoing structural and functional features described above, a method that can be implemented will be better appreciated with reference to FIGS. 4, 7, and 8. While, for purposes of simplicity of explanation, the method of FIGS. 4, 7 and 8 is shown and described as executing serially, it is to be understood and appreciated that such method is not limited by the illustrated order, as some aspects could, in other examples, occur in different orders and/or concurrently with other aspects from that shown and described herein. Moreover, not all illustrated features may be required to implement a method. The method or portions thereof can be implemented as instructions stored in one or more non-transitory storage media as well as be executed by a processing resource of a computer system, for example (e.g., one or more processor cores, such as the one or more processors 104 of the neural architecture system 100, as illustrated in FIG. 1, or the one or more processors of a related device 108, as illustrated in FIG. 1).

FIG. 4 depicts an example of a method 200 for transforming a connectivity matrix into a neural model. The method 200 can generate a neural model 112 and biomarker parameters 120 based on the neural activity data 21, such as illustrated in FIG. 1. At, 202, the neural activity data 21 can be generated. For example, the brain of the subject 24 can be scanned by the imaging device 20, such as shown in FIG. 1. In an example, the MRI scanner 22 can be configured to generate the MRI image data 36, such as illustrated in FIG. 2. In an alternative example, any device capable of generating neural activity of the subject 24 can be used. Thus, the neural activity data 21 can be generated by any currently existing (or future) device configured to generate neural activity data 21 based on the subject 24.

At 204, the neural activity data 21 can be preprocessed. For example, the neural activity data 21 can be preprocessed to remove noise and other undesired artifacts from the data collection. In some examples, preprocessing can be performed by the one or more processors 34 of the MRI scanner 22. Preprocessing can include, but not limited to, slice timing correction, removal of motion artifacts, noise reduction, extraction, segmentation, and smoothing, or the like. In an example, the fMRI and DTI images can be registered and scaled to an MRI image capturing the structure of the subject 24 or a structural model.

At 206, one or more region of interest (ROI) in the neural activity data 21 can be identified. The ROIs can correspond to any portion of the neural activity data 21 of known neurological importance such as, for example, based upon the activity of the subject 24 according to a task, or identified in an atlas derived for use in neuroscience. The atlas can be configured to integrate the results across different subject 24. For example, a common brain atlas can be used to adjust the neural activity data 21 to the atlas for comparative analysis. In some examples, the atlas can be defined according to a network approach. The network approach can delineate and investigate critical subnetworks of the brain such as, for example, the Default Mode Network (DMN), the Dorsal Attention Network, and the Frontoparietal Control Network. Network analysis can be used to investigate both the global and local structure of the brain, and the interaction of the networks with one another for individuals both at rest and during tasks.

Network investigations of neural connectivity can reveal organizing principles of the whole brain. First, the brain can be considered to be highly modular, e.g., the network can be well separated into densely connected subnetworks, as discussed above. Furthermore, brain networks can be hierarchically modular, e.g., subnetworks can be modular. Moreover, brain networks can demonstrate a "small world" structure: both strong clustering of regions within communities, and integration across these communities. This feature of brain networks can be considered as balancing local and global efficiency, and allowing the brain to minimize wiring costs. The brain can include a prevalence of "hub" regions: regions that are more highly interconnected with a large number of other regions than expected by chance. For example, brains can exhibit a "rich club" property of these hubs, where some hubs are highly interconnected with one another.

The ROIs can be used to analyze cognitive phenomenon that can include cognitive processes, cognitive deficits, and cognitive disorders. The network approach can be used to analyze cognitive processes such as, for example, learning, memory, cognitive control, emotion, and the like. Additionally, the network approach can identify network differences for individuals suffering from cognitive disorders such as, for example, schizophrenia, concussion, traumatic brain injury, multiple sclerosis, and so on.

The network approach to neuroscience can be broadly categorized according to the type of analysis at hand, including the analysis of (i) functional connectivity (e.g., correlations in signal across different regions), or (ii) structural connectivity (e.g., investigation of white matter tracks via DTI). It is noted that functional and structural analyses can be performed together. Functional connectivity can be further divided into investigations of participants at "rest"—performing no task aside from staying awake and referred to as resting state functional connectivity—and investigations of network activity while participants perform tasks. Task related investigations can detect modulations of network activity as a function of task, and individual differences. Moreover, the network activity during a task can be predictive of task performance.

Methods for quantifying network activity can include Psychophysiological Interaction (PPI), which can use functional connectivity between ROIs in order to examine the interplay of regions. The functional connectivity can be between a relatively small number of regions, or between a seed region and the entire rest of the brain. Other methods for investigating network structure, that do not require the specification of a seed region, an include independent components analyses (ICA) of time-series data to identify networks of regions that co-activate across a functional run. ICA methods can recover functional networks in a data-driven manner without using a predefined division of regions. This in turn allows for the probing of full functional networks rather than how a single region shifts connectivity with other regions.

Figure 5:
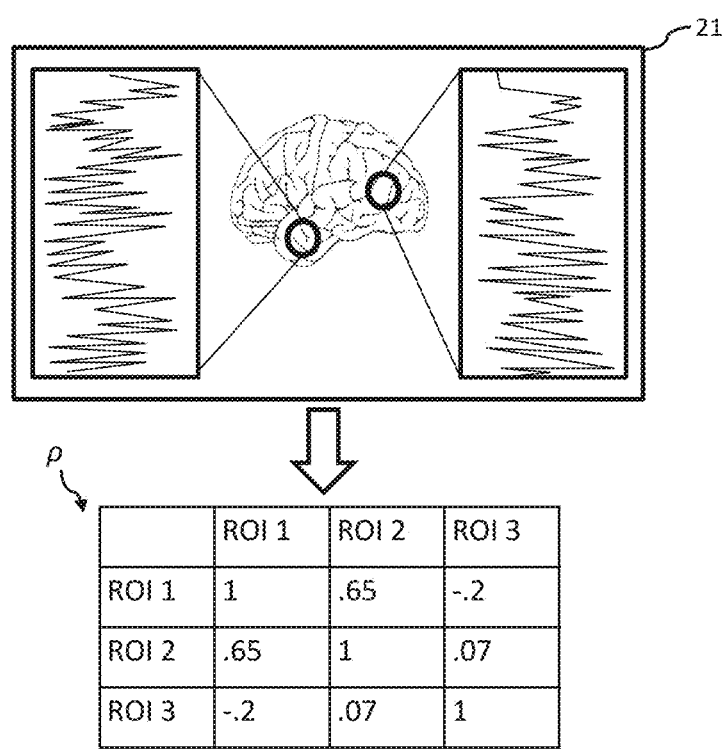
FIGS. 5 and 6 depict examples of a process for mapping neural activity data to a connectivity matrix.
Figure 6:
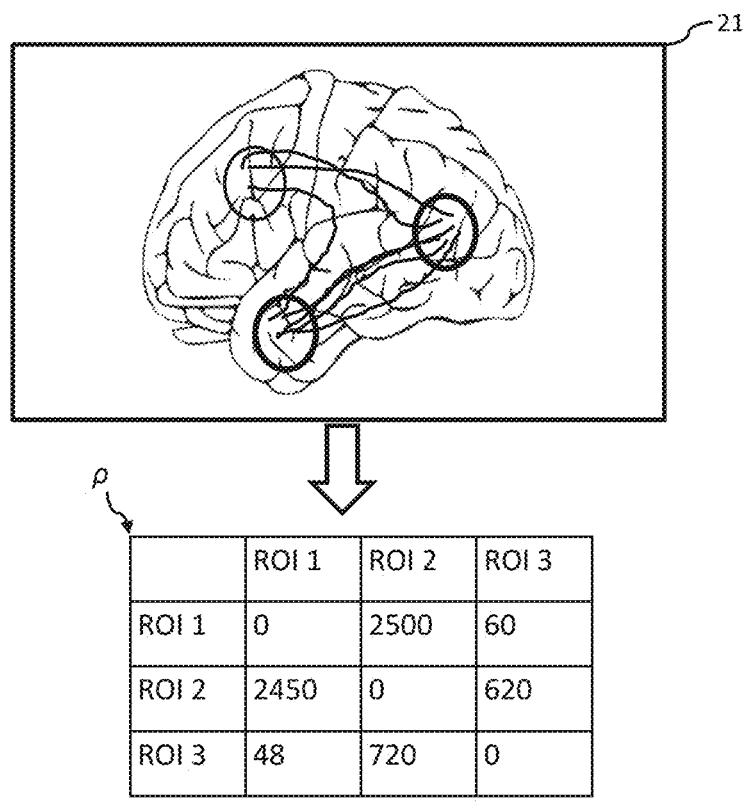

At 208, the connectivity matrix $\rho$ can be constructed based on the neural activity data 21. In some examples, the neural activity data 21 can be mapped to the connectivity matrix $\rho$ according to the atlas used for determining the ROIs as a weighted network. For example, as illustrated in FIG. 5, when the neural activity data 21 includes an fMRI image, the connectivity matrix $\rho$ can be provided as a correlation matrix. Alternatively, or additionally, as illustrated in FIG. 6, when the neural activity data 21 includes a DTI image, the connectivity matrix $\rho$ can be provided as the number of fiber tracks connecting the regions. In some examples, the weights of connectivity matrix $\rho$ can be scaled prior to being provided to the neural modeling engine 110, e.g., the weights can be scaled to lie between −1 and 1.

At 210, the connectivity matrix ρ can be analyzed, for example, by the neural modeling engine 110. As described herein, the neural modeling engine 110 can be defined according to endogenous statistics and exogenous statistics. Accordingly, the neural modeling engine 110 can be programmed to transform the connectivity matrix ρ into the neural model 112 representative of the neural activity data 21. Additionally, the neural modeling engine 110 can be programmed to transform the connectivity matrix ρ into biomarker parameters 120 corresponding to the endogenous statistics and exogenous statistics and representative of the neural activity data 21. In some examples, a joint modeling framework can be providing by combining connectivity matrices derived based on given ROIs (e.g., multiple distinct atlases). For example, a combined connectivity matrix can be created by combining the connectivity matrix ρ derived based on an MRI image with the connectivity matrix ρ derived based on an fMRI image.

FIG. 7 depicts an example of a method for generating a statistical cognitive model 122 of FIG. 1. The statistical cognitive model 122 can be used to predict cognitive phenomenon such as, for example, cognitive deficits, cognitive disorders, or both using the biomarker parameters 120. The method 220 can begin at 222 by collecting population data from one or more subjects 24. For example, instances of the neural activity data 21, the biomarker parameters 120, and cognitive phenomena data 124 can be collected to define a statistically significant population. The cognitive phenomena data 124 can include diagnosis of a particular cognitive phenomena that can correspond to the neural activity data 21. The neural activity data 21, the biomarker parameters 120, and the cognitive phenomena data 124 can be associated with one another such that each instance of data can be identified based upon another instance.

At 224, statistical distributions based on the biomarker parameters 120, and the cognitive phenomena data 124 can be generated. In some examples, the biomarker parameters 120 can be mapped to one or more probability density functions (PDFs), and tested for the ability of the biomarker parameters 120 to predict the associated cognitive phenomena data 124. PDFs that can reliably predict the demonstrate the cognitive phenomena data 124 based on the biomarker parameters 120 can be used to as the statistical cognitive model 122. In even further examples, the statistical cognitive model 122 can use multiple PDFs that can be combined via weighting or voting to predict a cognitive phenomenon, e.g., multiple biomarker parameters 120 can be used as input to predict a cognitive phenomenon. Moreover, a joint modeling framework can be provided by combining the biomarker parameters 120 derived based on the multiple atlases to generate the statistical cognitive model 122. Additionally, the method 220 can be repeated (e.g., iterated) as additional data becomes readily available. Accordingly, over time the power of the statistical cognitive model 122 can be substantially improved.

The statistical cognitive model 122 can be used to predict a cognitive phenomenon based on the biomarker parameters 120 of associated with the subject 24. For example, an instance of the biomarker parameters 120 according to a single test can be inputted to the statistical cognitive model 122. The statistical cognitive model 122 can output a probability according to the PDF associated with the statistical cognitive model 122. The probability can provide a quantitative assessment of the instance of the biomarker parameters 120. For example, an fMRI image can be analyzed statistically by the statistical cognitive model 122 for a particular cognitive disorder. Accordingly, a diagnosis can be provided along with an estimate of the severity of the diagnosis.

In some examples, the statistical cognitive model 122 can quantify the difference between normal and abnormal networks in the brain of the subject 24. For example, the biomarker parameters 120 associated with the subject 24 can be analyzed statistically by the statistical cognitive model 122. The statistical cognitive model 122 can output statistics corresponding to the difference between the biomarker parameters 120 of the subject 24 and the population used to generate the statistical cognitive model 122. Accordingly, the gap between normal networks of the subject 24 and abnormal networks of the population can be statistically quantified based on the biomarker parameters 120. Likewise, the gap between abnormal networks of the subject 24 and normal networks of the population can be statistically quantified based on the biomarker parameters 120. Accordingly, the biomarker parameters 120 can be used classify and quantify the result of network perturbations associated with cognitive phenomena such as, but not limited to, head trauma (e.g., concussions), Post-Traumatic Stress Disorder (PTSD), schizophrenia, and Alzheimer's.

Referring to FIG. 1, the quantitative gap can be reported to a clinician to assist with rapid clinical diagnosis of the degree of head trauma or other cognitive phenomena. For example, the subject 24 can be suspected of being suffering from a cognitive deficit or cognitive disorder. Neural activity data 21 can be collected from the subject 24. The neural activity data 21 can be communicated over the network 12 to the neural architecture system 100. The neural modeling engine 110 can be programmed to reduce the neural activity data 21 into the neural model 112 and biomarker parameters 120 useful for diagnosing the cognitive deficit or the cognitive disorder. As described herein, the biomarker parameters 120 can then be evaluated with the statistical cognitive model 122 to classify the cognitive deficit or cognitive disorder and quantify the severity of the cognitive deficit or cognitive disorder. The neural model 112, biomarker parameters 120, the classification and quantification, or combinations thereof can be communicated to the client device 108 associated with the clinician. Alternatively, or additionally, the client device 108 can be configured to execute the statistical cognitive model 122. Thus, the client device 108 can be provided with the biomarker parameters 120 and classify the cognitive deficit or cognitive disorder, and quantify the severity of the cognitive deficit or cognitive disorder.

Accordingly, the clinician can initiate a treatment plan (minimal-to-aggressive) based in part on severity of cognitive deficit or cognitive disorder. The use of the biomarker parameters 120 can be used to provide insight through the use of a large statistical population that is not available according to existing imaging modalities (e.g. MRI). For example, while the neural activity data 21 can be examined manually to reveal primarily anatomical changes, such anatomical changes may not be instructive in identifying many cognitive phenomena to the clinician. There can be substantial cognitive disruption in the absence of anatomical disruption (e.g. concussion). Moreover, the efficacy of the treatment plan can be monitored by periodically collecting new biomarker parameters 120 for evaluation with the statistical cognitive model 122. The classification and quantification of the cognitive deficit or cognitive disorder can track incremental changes that cannot be done practically via direct review of anatomical changes alone.

FIG. 8 depicts an example of a method 300 for analyzing a connectivity matrix for generating a neural model (e.g., the neural model 112, as illustrated in FIG. 1). The connectivity matrix can be analyzed with a neural model engine (e.g., the neural modeling engine 110, as illustrated in FIG. 1). The method can begin at 305 wherein neural activity data 21 can be transformed to [0, 1] based on topological statistics of a network associated with a brain of the subject 24. Prior to transformation of the neural activity data 21, the neutral activity 21 can be parameterized, as described herein. At, 310, parameters that maximize Equation 5 can be determined. For example, θ and β parameters can be evaluated such that Equation 5 is maximized (e.g., through alternating maximization of θ and β parameters, as described herein). The θ parameters are parameter estimates corresponding to endogenous network statistics.

The β parameters can be updated by applying Beta regression to estimate effects of exogenous covariates. Thus, parameters of exogenous covariates can be estimated. The θ parameters can be updated by simulating networks based on current estimates (e.g., via MCMC) for a plurality of N iterations, wherein N is an integer greater than one. During each iteration, noise can be added to create proposed networks, which can be evaluated relative to prior networks (or current networks). Such an evaluation can include calculating statistics of both networks and accepting or rejecting a given proposed network. The simulated networks can correspond to the denominator in Equation 2. The θ parameters can be identified that maximize a likelihood in Equation 5. At 315, a determination can be made if the θ parameters have changed by a given selected value. If the θ parameters have changed by the given selected value, the method can proceed to step 305. However, if the θ parameters have not changed by the given selected value, the method can proceed to 320. At 320, the neural model can be determined as converged, and results can be outputted. Accordingly, the neural model can be generated.

Example

Referring to FIGS. 1 and 3, an example of the neural modeling engine 110 according to the neuro-GERGM was evaluated to confirm a model fit. The example included using neural activity data 21 collected from resting state activity of a default mode network (DMN), and evaluated resting state functional connectivity (rsFC). Neural activity data 21 was collected from 250 subjects 24 that each completed a six-minute resting state scan in which their only task was to stay awake. Since excessive motion can introduce artificial correlations across regions in connectivity analyses, a strict movement cut-off was employed, which excluded any participant who moved greater than 2 millimeters (mm) while undergoing resting state. Further, some subjects 24 had their brain outside of the full field of view, and as such were excluded. Together, the study yielded neural activity data 21 for 154 total analyzable subjects 24.

Functional parcellation of the DMN was used to construct the connectivity matrix ρ. Since the parcellation contained only structures on the midline and left hemisphere, corresponding regions on the right hemisphere were used. Additionally, since there are asymmetries in the DMN across hemispheres, we adjusted the hotspots in the right hemisphere based on coordinates from NeuroSynth. As a result, a 20-node atlas was used.

The atlas was applied to the time-series fMRI data of each subject 24, such that each voxel within a region was averaged together, yielding 20 time-series' for each subject 24. The connection weights between regions of the connectivity matrix ρ was calculated with the Pearson correlation coefficient between pairs of regions, partialling out activity related to cerebrospinal fluid, white matter, and motion. This yielded a 20×20 symmetric matrices for each participant corresponding to the connection strength between each of the 20 regions. Finally, each participants' 20-node atlas was averaged to yield a single connectivity matrix ρ (e.g., a 20×20 matrix) that corresponded to the average connectivity across all subjects 24 in order to approximate an average brain. It is noted that such averaging was selected for model validation, and a strength of the examples described herein is the ability of recovering parameters for each individual, allowing for comparison across individuals (as well as within individuals across tasks).

In this example, 15 different models were fitted to the DMN. All statistics included an edges statistic (which corresponds to an intercept), and the remaining statistics corresponded to all 15 possible combinations of four statistics. Two of the statistics—two-stars and transitive triads—modeled endogenous statistics of the network. The other two statistics are exogenous statistics: the spatial distance between regions, and an indicator specifying whether or not two regions are in the same hemisphere of the brain (Hemisphere node match). T(·|β) was set as a Beta distribution, and the partial correlations were modeled as a regression on the exogenous predictors using Beta regression. Table 1, which is provided below, describes the predictors used in each of the models. To avoid model degeneracy, a geometric down weighting strategy was applied to the structural predictors. The strategy resulted in geometric down weights of 0.8 for two-stars and 0.4 for transitive triads.

TABLE 1

Description of network statistics and model specifications.

| Predictor | Description | Structural Model | Exogenous Model |
|---|---|---|---|
| Edges | Edge density of the network | ✓ | ✓ |
| Two - Stars | Density of two-stars. Measure of popularity of nodes | ✓ | ✓ |
| Transitive Triads | Density of triangles. Measure of clustering | | ✓ |
| Spatial distance | Euclidean distance between regions | | ✓ |
| Hemisphere node match | Indicator specifying if two regions are in the same hemisphere | | ✓ |

The neuro-GERGM output both a parameter estimate and a standard error for each statistic specified. The coefficient outputs of the statistics can be found in Table 2. Across all statistics, a significantly negative two-stars coefficient, and a significantly positive transitive triads coefficient was determined. Further, the statistics were relatively unchanged with the addition of the exogenous covariates. Together, this suggests that, at least for the present atlas, the DMN displays more triadic closure (e.g., clustering) than would be expected by chance, but less preferential attachment (e.g., the use of hubs) than would be expected by chance.

TABLE 2

Network output coefficients, numbers in parentheses correspond to standard errors.

| | Edges | Two-Stars | Transitive Triads | Hemisphere | Distance |
|---|---|---|---|---|---|
| Endogenous | .24(.02) | −.44(.11) | .22(.05) | | |
| Exogenous | .86(.10) | −.45(.11) | .21(.05) | .06(.024) | .08(.02) |

To assess whether the structural features were recovered, t-tests were conducted to determine whether the distribution mean was significantly different from the observed value. In this example, higher p-values are desired, as they suggest that the two means are not statistically different from one another (e.g., better fit). The endogenous statistics produced simulated networks that were statistically indistinguishable for the two-stars statistic (p=0.99) and the network density (p=0.40) statistic, but not ttriads (p=0.02). The exogenous statistics, on the other hand, produced simulated networks that were statistically indistinguishable for all three statistics (two-stars: p=0.66; ttriads: p=0.47; density: p=0.30).

In another set of experiments, we have modeled additional subnetworks within the brain and found largely consistent findings in regards to the organizational factors. In this investigation, we used a functional atlas that provides subnetwork groupings for each of 264 brain regions. Of these networks, we modeled 9 different subnetworks, including a Dorsal Attention Network, a Frontoparietal Control Network, a Ventral Attention Network, a Visual Network, an Auditory Network, a Reward Network, a Subcortical Network, a Salience Network. The size of the subnetworks range in size from 9 nodes to 31 nodes. Across all of these subnetworks, we find either a significantly negative two-stars statistic (or a directional but non-significant effect), and a significantly positive triads statistic (or a directional but non-significant effect).

In another demonstration, we have recently applied the descriptive statistics approach to investigating schizophrenia. Specifically, we took a dataset with 145 individuals (both schizophrenics and healthy controls) who underwent 6 minutes of resting state fMRI. For each participant, we constructed a weighted correlation matrix, and calculated the following weighted descriptive statistics: clustering, eigenvector centrality, betweenness centrality, closeness centrality, and degree centrality. We input these metrics into a machine-learning algorithm, and developed a classifier that could predict with 75-85% cross-validation accuracy whether an individual was healthy or schizophrenic.

It should now be understood that the examples provided herein can conduct statistical inference and hypothesis testing on neurological network data without departing from the basic structure of the data. For instance, the neuro-GERGM can be used to evaluate neural activity data (e.g., fMRI images, DTI images, or both) to generate parsimonious and well-fitting models of neurological networks. Additionally, the dimensionality of the intractable problem of comparing neural activity data across multiple subjects can be reduced from a large dimension problem (e.g., about 100K dimension) to a small dimension problem (e.g., between about 3-8 dimensions). For example, the use of the biomarker parameters for cross and intra network comparisons can substantially reduce the memory and processing requirements for modeling cognitive phenomena.

Additionally, the neuro-GERGM can quantify the intrinsic architecture of neural networks in a manner that does not require the reduction or censoring of data. For example, the neuro-GERGM can probe the functional organization of the brain to produce well-fitting models that capture the structural properties of neurological networks, and predict features of an out of sample network with high accuracy.

It is noted that the terms "substantially" and "about" can be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

What have been described above are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A computer-implemented method comprising:
   identifying, by one or more processors, regions of interest of a brain of a subject based on image data characterizing the brain of the subject, wherein the image data comprises one of magnetic resonance imaging (MRI) data, functional magnetic resonance imaging (fMRI) image data, diffusion weighted imaging (DWI) data, diffusion tensor imaging (DTI) data, electromyogram (EMG) data, electroencephalogram (EEG) data, positron emission tomography (PET) data, magnetoencephalography (MEG) data, Electrocorticography (ECoG), ultrasound imaging data, and a combination thereof;
   mapping, by the one or more processors, the regions of interest of the image data to a connectivity matrix, wherein the connectivity matrix is a weighted and directed or undirected network;
   transforming, by the one or more processors, the connectivity matrix into a biomarker parameter, wherein the biomarker parameter corresponds to a defined statistic;
   analyzing, by the one or more processors, the biomarker parameter according to a probability density function of a statistical cognitive model, wherein the probability density function maps a separate population of the biomarker parameter to a cognitive phenomenon; and
   generating, by the one or more processors, a probability of the cognitive phenomenon based on the probability density function of the statistical cognitive model, wherein the probability quantifies a severity of the cognitive phenomenon.

2. The computer-implemented method of claim 1, wherein the biomarker parameter corresponds to a first biomarker parameter, and wherein the statistical cognitive model comprises an additional probability density function that maps a second biomarker parameter to the cognitive phenomena.

3. The computer-implemented method of claim 2, wherein the first biomarker parameter and the second biomarker parameter are computed, by the one or more processors, based on different atlases such that the statistical cognitive model provides a joint modeling framework.

4. The computer-implemented method of claim 1, wherein transforming, by the one or more processors, the connectivity matrix into the biomarker parameter is according to a neurological generalized exponential random graph model (neuro-GERGM) algorithm.

5. The computer-implemented method of claim 1, further comprising administering a treatment for the cognitive phenomenon according to the severity of the cognitive phenomenon.

6. The computer-implemented method of claim 1, wherein the statistic comprises one of an endogenous statistic, an exogenous statistic, and a combination thereof.

7. A method comprising:
receiving, at one or more processors, image data of a subject;
transforming, at the one or more processors, the image data with a neural modeling engine into a biomarker parameter, wherein the biomarker parameter corresponds to a defined statistic;
analyzing, at the one or more processors, the biomarker parameter with a probability density function of a statistical cognitive model, wherein the probability density function maps a separate population of the biomarker parameter to a cognitive phenomenon;
generating, at the one or more processors, an initial probability of the cognitive phenomenon based on the probability density function of the statistical cognitive model; and
quantifying, at the one or more processors, a severity of the cognitive phenomenon for the subject based upon the initial probability.

8. The method of claim 7, further comprising administering a treatment for the cognitive phenomenon based on the severity of the cognitive phenomenon.

9. The method of claim 8, further comprising:
receiving, at the one or more processors, subsequent image data of the subject;
transforming, at the one or more processors, the subsequent image data with the neural modeling engine into a subsequent biomarker parameter, wherein the subsequent biomarker parameter corresponds to a different defined statistic;
generating, at the one or more processors, a subsequent probability of the cognitive phenomenon based on the probability density function of the statistical cognitive model;
comparing, at the one or more processors, the initial probability and the subsequent probability; and
determining, at the one or more processors, an efficacy of the treatment based on a result of the comparison.

10. The method of claim 7, wherein the neural modeling engine comprises a neurological generalized exponential random graph model (neuro-GERGM) algorithm.

11. The method of claim 7, wherein the image data comprises one of functional magnetic resonance imaging (fMRI) data, diffusion weighted imaging (DWI) data, diffusion tensor imaging (DTI) data, electromyogram (EMG) data, electroencephalogram (EEG) data, positron emission tomography (PET) data, magnetoencephalography (MEG) data, Electrocorticography (ECoG) data, ultra-sound imaging data, and a combination thereof.

12. The method of claim 7, wherein the statistic comprises one of an endogenous statistic, an exogenous statistic, and a combination thereof.

* * * * *